Figure 1:
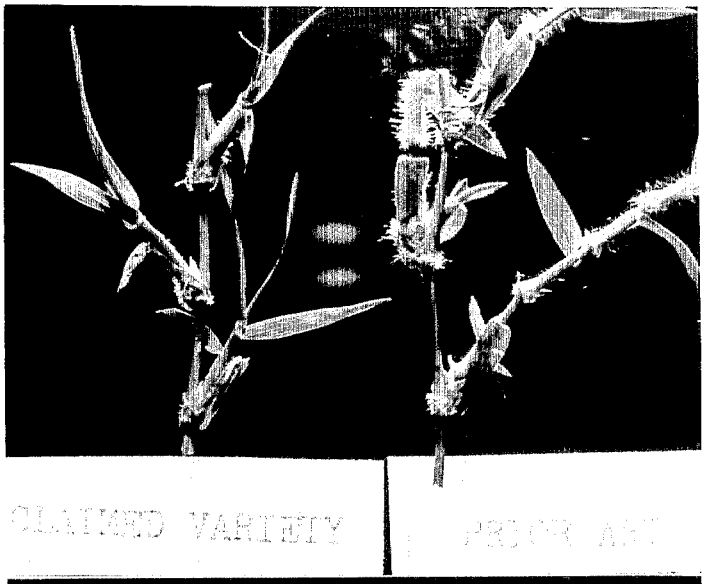

United States Patent [19]

Whiting

[11] Patent Number: Plant 5,689

[45] Date of Patent: Mar. 11, 1986

[54] DIGITARIA DIDACTYLA GRASS PLANT

[76] Inventor: Hubert F. Whiting, 2644 Via Alicia, Fallbrook, Calif. 92028

[21] Appl. No.: 609,869

[22] Filed: May 14, 1984

[51] Int. Cl.[4] ..... A01H 5/12

[52] U.S. Cl. ..... Plt./88

[58] Field of Search ..... Plt/88

*Primary Examiner*—Robert E. Bagwill

[57] ABSTRACT

I disclose that my herein invention of a new variety of Digitaria Didactyla grass plant was discovered by me through my cross-pollinating selected varieties of Digitaria Didactyla grass plant then through asexual repropagation selected the new and distinct variety of Digitaria Didactyla grass plant which produces an excellent turfgrass of a finer more uniform and smooth texture, the color of the grass is a dark green color as defined in ISCC-NBS Centroid color chart; the stigmas of the new variety of Digitaria Didactyla grass plant are deep purplish pink color as defined in the ISCC-NBS Centroid color chart; the anthers of the new variety of Digitaria Didactyla grass plant are dark red color as defined in the ISCC-NBS Centroid color chart; the new variety of Digitaria Didactyla grass plant is glabrous except for a few hairs around the stolon and culm nodes and has a finer texture.

3 Drawing Figures

The present invention and discovery relates to a new and distinct variety of Digitaria Didactyla grass plant which was discovered by me through cross-pollination of collected varieties of Digitaria Didactyla grass plants. This cross-pollination was done by me at Indio, Calif., about 34 degrees north latitude. I harvested seeds from this cross-pollination of the selected varieties of Digitaria Didactyla grass plants and planted these seeds out in germinating trays. Shortly after the seeds germinated, I transplanted each separate seedling into one gallon containers. There were 331 of these seedlings planted out by me in this way. As these seedlings grew and matured, I selected the most desirable for turfgrass potential. This left 105 seedlings. These 105 seedlings were then each individually broken up by me into small pieces of stolons, then I planted these small pieces of stolons into the soil in an area that was three feet square. When this process was completed, I had 105 individual seedlings planted in 105 three foot square plots, all asexually transplanted by me. The location of this transplanting was at Fallbrook, Calif. Once these 105 three foot square plots became established through the spreading of the planted stolons, I formed a turfgrass surface through regular mowing. I again made selections from the 105 plots. The selections I made this time were again individually transplanted by me asexually by breaking sufficient stolon material of each separate selection to further replant the now 23 selections into larger individual separate plots of ten feet by eight feet. Once these larger plots became established through the spreading of the planted stolons I formed a turfgrass surface through regular mowing. I again made selections from these 23 plots. The new claimed variety of Digitaria Didactyla grass plant is one of those selections, and its designation is D-13. This new selected variety of Digitaria Didactyla grass plant spread by stolons to produce an excellent turfgrass surface when regularly mown. I then asexually transplanted this new claimed variety of Digitaria Didactyla grass plant into replicated randomized plots and, after complete establishment and regular mowing, I observed that this new claimed variety of Digitaria Didactyla grass plant produced a very dark green uniform smooth fine textured surface excellent for golf putting greens. The uniformity of texture and color was superior to the closest known variety of Digitaria Didactyla grass plant. During the continued asexual reproduction by stolons, I have confirmed that the above-described characteristics are transmitted through succeeding propagations, and have confirmed that the new variety of Digitaria Didactyla grass plant has the following unique combination of characteristics. The new and distinct variety of Digitaria Didactyla grass plant is illustrated in the accompanying color photographs, with photographs of the closest known Digitaria Didactyla grass plant. The most noticeable variations between the claimed variety of Digitaria Didactyla grass plant and the closest known variety is that the claimed variety is a darker green color of a more uniform and even texture with stigmas deep purplish pink color and anthers of dark red color. The new claimed variety of Digitaria Didactyla grass plant is glabrous except for a few hairs around the stolon and culm nodes.

IN THE DRAWINGS

FIG. 1 is a photograph of two culms taken from the same test area, one piece is of the new and distinct variety of Digitaria Didactyla grass plant, the other piece of culm is of the closest-known variety of Digitaria Didactyla grass plant (identified by prior art). This photograph shows the new claimed variety of finer longer leaf blades.

Figure 2:
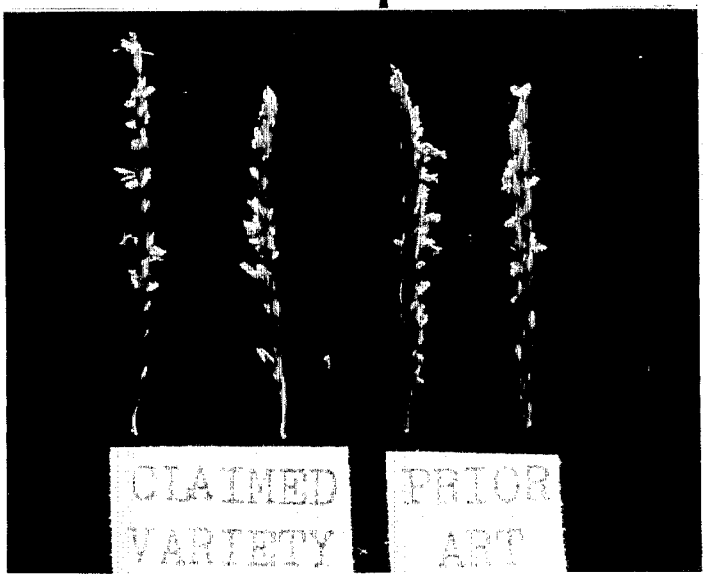

FIG. 2 is a photograph of spikes taken from the same test area of the new claimed variety of Digitaria Didactyla grass plant, and the closest-known variety of Digitaria Didactyla grass plant (identified by prior art). This photograph shows the deep purplish pink colored stigmas, Color Number 248.d.pk. of the ISCC-NBS Centroid color chart, of the new claimed variety of Digitaria Didactyla grass plant, compared to the closest-known variety of Digitaria Didactyla grass plant, which has dark red colored stigmas, Color Number 16.d.red of the ISCC-NBS Centroid color chart.

Figure 3:
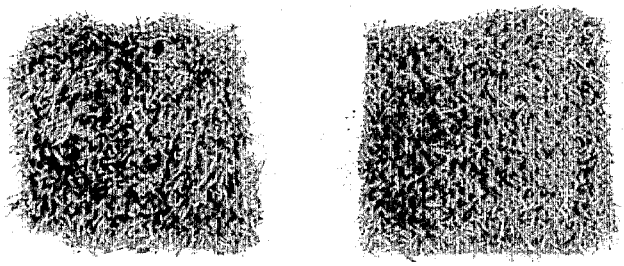

FIG. 3 is a photograph of a top view of sod pieces taken from the same test area of the new claimed variety of Digitaria Didactyla grass plant and the closest known variety of Digitaria Didactyla plant (identified by prior art) which sod pieces have been subject to the same mowing conditions at virtually the same time with identical maintenance procedures. This photograph shows a finer more uniform texture with a darker green color, Color Number 146.d.g. of the ISCC-NBS Centroid color chart compared to the closest known variety of Digitaria Didactyla grass plant (identified by prior art) which is more coarse and not as uniform textured with a moderate yellowish green color, Color Number 136.m.yg. of the ISCC-NBS Centroid color chart.

A detailed description of the new distinct variety of Digitaria Didactyla grass plant is:

(a) An attractive, dark green color, Color Number 146.d.g. of the ISCC-NBS Centroid color chart.

(b) The grass is low-growing, erect in habit.

(c) The grass spreads by stolons and rhizomes, forming a dense, uniform surface with an extensive root system.

(d) Culms vary in height from 6–30 centimeters.

(e) Leaves rolled in bud shoot.

(f) The blade is V-shaped in cross-section, keeled and gradually tapering to an acute point.

(g) The first mature leaf is 2–2.5 millimeters in width and 25–70 millimeters in length.

(h) The leaf blade is glabrous, except at the base of the leaf close to the ligule, where a few hairs are present.

(i) The ligule is membranous acute and medium in height.

(j) Auricles are absent.

(k) The collar is narrow.

(l) The sheath is glabrous, split with margins overlapping.

(m) The entire plant is glabrous, except on the upper leaf surface, near the ligule on top of the sheath around the internodes.

(n) Inflorescence consists of 2–3 spikes at the top of the main stem, deflexed at maturity from 25–45 millimeters long.

(o) The spikelets are glabrous in two rows 2–3 millimeters long, blunt at their base, pointed at their tips, borne singly on short branches and blumes are present; the spikelet contains stigmas of deep purplish pink, Color Number 248.d.pk. of the ISCC-NBS Centroid color chart, and anthers of dark red, Color Number 16.d.red of the ISCC-NBS Centroid color chart.

A detailed description of the closest known variety of the species of Digitaria Didactyla grass plant is:

By comparison, the closest known variety of the species is described as prior art in my U.S. Plant Pat. No. 5,194 dated Feb. 21, 1984, the description of this closest known variety is the variety of the species is a lower growing erect in habit of a moderate yellowish-green color, Color Number 136.m.yg. of the ISCC-NBS Centroid color chart; culms vary in height from 5–25 centimeters in length; the first mature leaf is 3–3.5 millimeters in width, 25–75 millimeters in length; the blade is glabrous except near the ligule where a few hairs are present; the ligule is membranous acute and medium in height. The sheath is split pubescent very dense pubescent around the node area. The spikelet contains light yellowish-brown colored anthers Color Number 76.1.ybr. of the ISCC-NBS Centroid color chart with deep purplish-red colored stigmas Color Number 256.deep pr. of the ISCC-NBS Centroid color chart.

Having now described the new and distinct variety of Digitaria Didactyla grass plant which I have discovered and asexually reproduced, I claim:

1. A new variety of Digitaria Didactyla grass plant herein shown and described by a dark green color as defined by the ISCC-NBS Centroid color chart; this new variety produces a more uniform smoother finer textured surface; the anthers are a dark red as defined by the ISCC-NBS Centroid color chart; the stigmas are of a deep purplish pink as defined by the ISCC-NBS Centroid color chart.

* * * * *

PRIOR ART

CLAIMED VARIETY